United States Patent
Sexton (10) Patent No.: US 9,733,202 B2
(45) Date of Patent: Aug. 15, 2017

(54) WIRELESS SENSOR AND METHOD OF INTERROGATING THEREOF

(71) Applicant: General Electric Company, Schenectady, NY (US)

(72) Inventor: Daniel White Sexton, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 44 days.

(21) Appl. No.: 14/816,646

(22) Filed: Aug. 3, 2015

(65) Prior Publication Data

US 2017/0038323 A1 Feb. 9, 2017

(51) Int. Cl.
*G01R 27/04* (2006.01)
*G01N 27/02* (2006.01)

(52) U.S. Cl.
CPC .................. *G01N 27/023* (2013.01)

(58) Field of Classification Search
CPC ............. A61B 5/0031; A61B 2562/02; A61B 2562/0219; A61B 2562/0261; A61B 5/0215; A61B 5/103; A61B 5/6846; A61B 5/726; A61B 2017/00022; A61B 2034/2051; A61B 2090/3954; A61B 2090/3958; A61B 34/20; A61B 90/36; H02J 7/025; H02J 5/005; H02J 50/12; H02J 50/23; G01L 1/00; G01L 7/00; G01L 1/144; G01N 27/9046; H01F 2017/006;

(Continued)

(56) References Cited

U.S. PATENT DOCUMENTS 4,551,801 A 11/1985 Sokol
4,801,885 A * 1/1989 Meissner ........... G01R 33/3657
324/318

(Continued)

FOREIGN PATENT DOCUMENTS

WO 0197556 A2 12/2001

OTHER PUBLICATIONS

Hamsch et al., "An Interrogation Unit for Passive Wireless SAW Sensors Based on Fourier Transform", IEEE Transactions on Ultrasonics, Ferroelectrics, and Frequency Control, vol. 51, No. 11, Nov. 2004, pp. 1449-1456.

*Primary Examiner* — Vinh Nguyen
(74) *Attorney, Agent, or Firm* — Ziolkowski Patent Solutions Group, SC; Jean K. Testa (57) ABSTRACT

A wireless sensor array communication system includes a plurality of wireless sensors each including a resonant circuit that is excited by an RF pulse so as to provide a resonant energy proportional to a measurand being monitored. A transceiver of an interrogator system transmits RF pulses to each of the sensors to excite the resonant circuits therein and receives RF signals transmitted from each of the sensors that are indicative of the resonant energy provided by the resonant circuit. A magnet-gradient coil arrangement of the interrogator system generates a magnetic field and selectively applies magnetic field gradients along a number of axes, such that a frequency and phase of the resonant energy provided by the resonant circuit of each wireless sensor is altered responsive thereto, with the altered frequency and phase of the resonant energy being a function of a location of the respective wireless sensor within the magnetic field.

20 Claims, 2 Drawing Sheets

(58) Field of Classification Search
CPC .............. H01F 41/042; H01F 17/0006; H01F 2027/2809; H01F 27/2804; H01F 38/14; Y10T 29/49016; Y10T 29/49103; A61N 1/056; A61N 1/362; G06K 19/0717; G06K 19/0723
See application file for complete search history.

(56) References Cited

U.S. PATENT DOCUMENTS

| | | | |
|---|---|---|---|
| 5,581,257 A * | 12/1996 | Greene | C30B 33/00 235/375 |
| 6,011,393 A * | 1/2000 | Kaufman | G01R 33/34046 324/318 |
| 6,720,887 B1 | 4/2004 | Zunti | |
| 7,500,379 B2 | 3/2009 | Hines | |
| 7,642,898 B1 | 1/2010 | Malocha et al. | |
| 8,175,839 B2 | 5/2012 | Kurtz et al. | |
| 8,717,146 B2 | 5/2014 | Potyrailo et al. | |
| 2005/0210340 A1* | 9/2005 | Townsend | G08C 17/02 714/701 |
| 2013/0181573 A1 | 7/2013 | Hines et al. | |

* cited by examiner

WIRELESS SENSOR AND METHOD OF INTERROGATING THEREOF

BACKGROUND OF THE INVENTION

Embodiments of the invention relate generally to resonant sensors and, in particular, to resonant sensors that may be interrogated via the use of a combination of RF pulses and a magnetic field gradient being applied thereto, such that a resonant sensor will emit a unique phase and frequency pair based on it's positioning within the magnetic field.

Resonant sensors are sensors whose output can vary with respect to changes in specific environmental or biological conditions present near the resonant sensor. Typically, resonant sensors are comprised of an inductance-capacitance (LC) circuit with a specific resonance frequency. The resonant sensor is excited by an RF pulse and then its value can be read back by the amount of energy they emit as the LC circuit's resonant energy decays. In use, the amount of energy imparted into the resonant circuit can be proportional to the measurand (i.e., the object/substance being measured) and/or the frequency of resonance in the resonant circuit can be altered by the measurand. A readout of a resonant sensor can then be performed via a receiver that records the energy emitted from the sensor.

While use of a single resonant sensor raises no issues with regard to interrogation of the sensor and readout of the sensor via an associated receiver, it is recognized that issues arise when a sensor array composed of a large number of resonant sensors (e.g., 1000+ sensors) in close proximity to one another are to be interrogated and read out. That is, it is challenging to differentiate the response from each resonant sensor from the other proximate sensors such that the readout information from each respective sensor can be separated.

Several techniques have been employed in order to solve the problem of uniquely identifying sensors in a large sensor array. One common solution is for each sensor in the sensor array to be specifically designed to respond to a unique frequency or respond to a unique wave form (coding). However, this makes every sensor unique and leads to increased cost in manufacturing and providing the sensors for the sensor array. Another common solution is for each sensor to include complex electronics to harvest power from the RF interrogation signal, perform signal processing, and transmit a unique signal from the sensor. However, due to the amount of energy required for such electronics, a large antenna or coil is needed in the sensor that increases the size of the sensor. Additionally, the complex electronics in the sensor increases the cost in manufacturing and providing the sensors for the sensor array.

Therefore, it is desirable to provide a resonant sensor that is configured so as to enable the sensor to be uniquely identified and differentiated from other resonant sensors in a sensor array. It is further desirable that such a resonant sensor would have a common construction with other resonant sensors in a sensor array and not require complex signal processing electronics therein, such that the cost and complexity of the resonant sensor is minimized.

BRIEF DESCRIPTION OF THE INVENTION

In accordance with one aspect of the invention, a wireless sensor array communication system includes a sensor array composed of a plurality of wireless sensors, each of the plurality of wireless sensors comprising a resonant circuit that is excited responsive to an RF pulse received by the wireless sensor such that the resonant circuit provides a resonant energy, with a characteristic of the resonant energy being proportional to a measurand monitored by the passive wireless sensor. The wireless sensor array communication system also includes an interrogator system having a transceiver in operable communication with each of the plurality of wireless sensors in the sensor array, with the transceiver configured to transmit RF pulses to each of the plurality of wireless sensors to excite the respective resonant circuits therein and receive RF signals transmitted from each of the plurality of wireless sensors in the sensor array, each of the RF signals being indicative of the resonant energy provided by the resonant circuit. The interrogator system further includes a magnet-gradient coil arrangement configured to generate a magnetic field and selectively apply magnetic field gradients to the magnetic field along a number of axes. Each of the plurality of wireless sensors is configured such that a frequency and phase of the resonant energy provided by its respective resonant circuit, and included in the RF signal transmitted therefrom, is altered responsive to the generated magnetic field and the applied magnetic field gradients, the altered frequency and phase of the resonant energy being a function of a location of the respective wireless sensor within the magnetic field.

In accordance with another aspect of the invention, a method of interrogating a plurality of wireless sensors in a sensor array includes wirelessly transmitting an RF pulse from a transceiver to each of the plurality of wireless sensors in the sensor array, the RF pulse exciting a resonant circuit included in each of the plurality of wireless sensors so as to cause the resonant circuit to generate a resonant energy. The method also includes applying a magnetic field to a volume including the sensor array via a magnet, applying a magnetic field gradient to the magnetic field along a first axis via activation of a first gradient coil, applying a magnetic field gradient to the magnetic field along a second axis via activation of a second gradient coil, and wirelessly transmitting RF signals from each of the plurality of wireless sensors in the sensor array as sensor outputs to the transceiver, with the RF signal transmitted from each respective wireless sensor indicative of the resonant energy generated by its respective resonant circuit. Application of the magnetic field gradient along the first and second axes causes a frequency and phase of the RF signal generated by each respective wireless sensor of the plurality of wireless sensors to be altered as a function of a location of the respective wireless sensor within the volume to which the magnetic field is applied.

In accordance with yet another aspect of the invention, a passive wireless sensor includes an antenna configured to receive RF interrogation pulses and transmit RF signals and a resonator circuit operably connected to the antenna and that is excited responsive to RF interrogation pulses received by the antenna, the resonator circuit configured to generate a resonant energy responsive to an RF interrogation pulse, with the resonant energy being proportional to a parameter monitored by the passive wireless sensor. The passive wireless sensor also includes a magnetic component incorporated into the resonator circuit that is sensitive to a magnetic field such that a material characteristic of the magnetic component is altered when exposed to a magnetic field, with the magnetic component being constructed so as to alter a frequency of the resonant energy generated by the resonator circuit when selectively exposed to a magnetic field and magnetic field gradients, wherein the altering of the frequency and phase of the resonant energy is based on a local magnetic field strength of the magnetic field at a location of the passive wireless sensor within the magnetic field.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Embodiments of the invention provide an array of resonant sensors that may be interrogated via the use of a combination of RF pulses and a magnetic field gradient being applied thereto. The interrogation of the array of sensors using the combination of RF pulses and the magnetic field gradient results in each resonant sensor emitting a unique phase and frequency pair based on its positioning within the magnetic field, so as to enable the reading of each sensor to be separated at a receiver.

Figure 1:
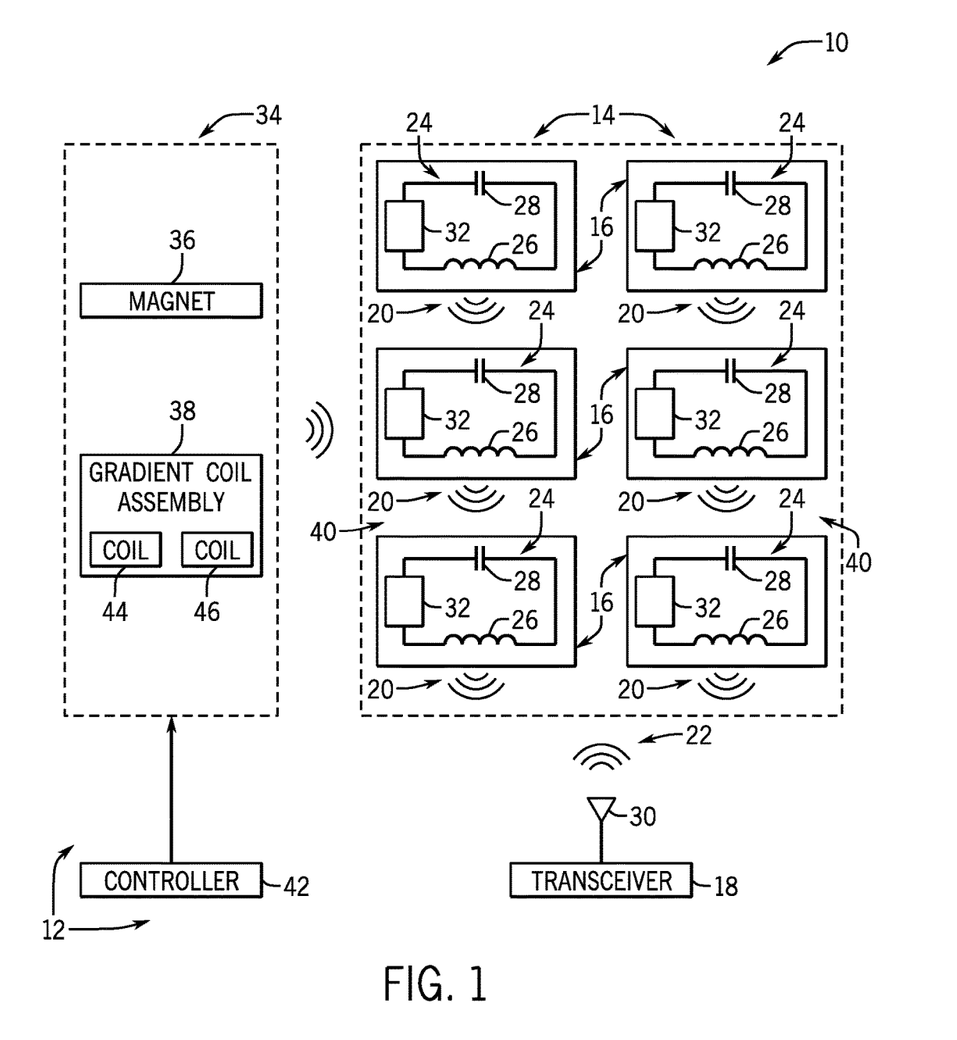
FIG. 1 is a block schematic diagram of a passive wireless sensor array communication system in accordance with an embodiment of the invention.

Referring now to FIG. 1, a block schematic diagram of a passive wireless sensor array communication system 10 is shown according to an embodiment of the invention. The communication system 10 includes a sensor interrogator system 12 and a sensor array 14 comprised of a plurality of wireless sensors 16 that are provided for sensing a specific parameter or measurand—with examples of such parameters being neural activity, pressure, temperature, acceleration, angular rate, PH level, glucose level, salinity, viscosity, dielectric constant, humidity, proximity, electrolyte level, and oxygen level. While only six sensors 16 are shown as being included in the sensor array 14, it is recognized that the actual number of sensors included in the array could be much higher, such as an array of 1000+ sensors used for measuring neural activity, for example. The interrogator system 12 includes a transceiver 18 therein in operable and remote communication with each of the plurality of wireless sensors 16 in the sensor array 14, with the transceiver 18 configured to transmit signals to the sensors 16 and receive signals therefrom. The transceiver 18 is capable of exciting the sensors 16 by transmitting a signal, such as a radio frequency ("RE") pulse, at or near the resonant frequency of the sensors 16. (See FIG. 1.) The sensors 16 may emit an RE ring signal—indicated at 20—for a short period of time in response to the excitation pulse from the transceiver 18.

Each sensor 16 may be a passive device, containing no power source of its own, and capable of emitting an RE ring signal 20 in response to an excitation/interrogation signal—indicated at 22—at or near the resonant frequency of the sensor 16. The sensor 16 may include a resonant circuit 24 comprised of a inductor 26 and a capacitor 28 whose inductance or capacitance varies based on the sensed parameter/measurand (e.g., brain neural activity), with the varying capacitance or inductance altering the resonant frequency of the resonant circuit 24 of sensor 16. To vary the resonant frequency of the resonant circuit 24 of the sensor 16 in proportion to the sensed parameter, either inductor 26 or capacitor 28, or both, may be configured to change inductance or capacitance proportionately with the sensed parameter. In an example embodiment shown in FIG. 1, capacitor 28 is fixed and inductor 26 is variable. However, while the sensor 16 is described as an RF resonant sensor that includes an inductor 26 and a capacitor 28, it should be appreciated that the sensor 16 may have a different suitable construction, such as being in the form of a cavity resonator, for example, or other similar sensor known in the art. It is also recognized that, in addition to or rather than the frequency of the resonant circuit 24 being set by the measurand, the amount of energy imparted into the resonant circuit 24 can be proportional to the measurand.

In the embodiment of FIG. 1, the inductor 26 in each sensor 16 also functions as an antenna for its respective sensor 16, coupling energy to and from another antenna 30 located on the transceiver 10. The transceiver 18 may excite each of the sensors 16 in the sensor array 14 by transmitting an excitation/interrogation pulse 22 in the vicinity of the sensor 16. For example, the reader may emit an RF excitation pulse 22 at or near the resonant frequency of the sensors 16. The sensors 16 may then each emit an RE signal 20 in response to the excitation RE pulse 22. The transceiver 18 may determine the frequency of the RF ring signals 20 in order to determine the sensed parameter value from each sensor 16.

As shown in FIG. 1, the resonant circuit 24 of each sensor 16 further includes a magnetic component 32 incorporated therein that is able to selectively alter operation of the sensor 16. The magnetic component 32 is constructed so as to be sensitive to a magnetic field, such that a material characteristic of the magnetic component 32 is altered when exposed to the magnetic field. In an exemplary embodiment, the magnetic component 32 is constructed of a resonant material whose inductance is altered when selectively exposed to a magnetic field, with the altering of the inductance being based on a local magnetic field strength of the magnetic field at a location of the sensor 16 within the magnetic field. The altered inductance of the component 32, and in turn the altered inductance of resonant circuit 24, causes a frequency of the resonant energy generated by the resonant circuit 24 to also be altered, such that the frequency in the RF ring signal 20 provided to the transceiver 18 is changed when the sensor 16 is exposed to a magnetic field and magnetic field gradients.

In order to provide for selective application of a magnetic field and magnetic field gradients to a volume in which the sensor array 14 is contained, a magnet—gradient coil arrangement 34 (composed of a polarizing magnet 36 and a gradient coil assembly 38) is included in the interrogator system 12 that is configured to generate a magnetic field and selectively apply a magnetic field gradient to the magnetic field along a number of axes. That is, magnet 36 generates a uniform magnetic field (polarizing field $B_0$) for a volume 40 in which the sensor array 14 is contained, while individual gradient coils in the gradient coil assembly 38 may be excited by respective gradient amplifiers (not shown) to produce magnetic field gradients that will be used for spatially encoding RF ring signals generated by the sensors 16 of sensor array 14 so that each RF signal can be related to an exact location, as will be explained in greater detail below.

The magnet—gradient coil arrangement 34 may be controlled by a controller 42 operably connected thereto. The controller 42 may control operation of magnet 36 to selectively generate the polarizing field $B_0$ and may send control signals to the gradient coil assembly 38 that indicate the timing and shape of gradient pulses to be produced by the gradient coils. More specifically, the controller 42 sends control signals to the gradient coil assembly 38 that selectively excite particular gradient coils in the gradient coil assembly at a designated time—with at least a first gradient coil 44 and a second gradient coil 46 of the gradient coil assembly 38 selectively generating a magnetic field gradient along a first axis and along a second axis at designated times, as will be explained in greater detail below.

Figure 2:
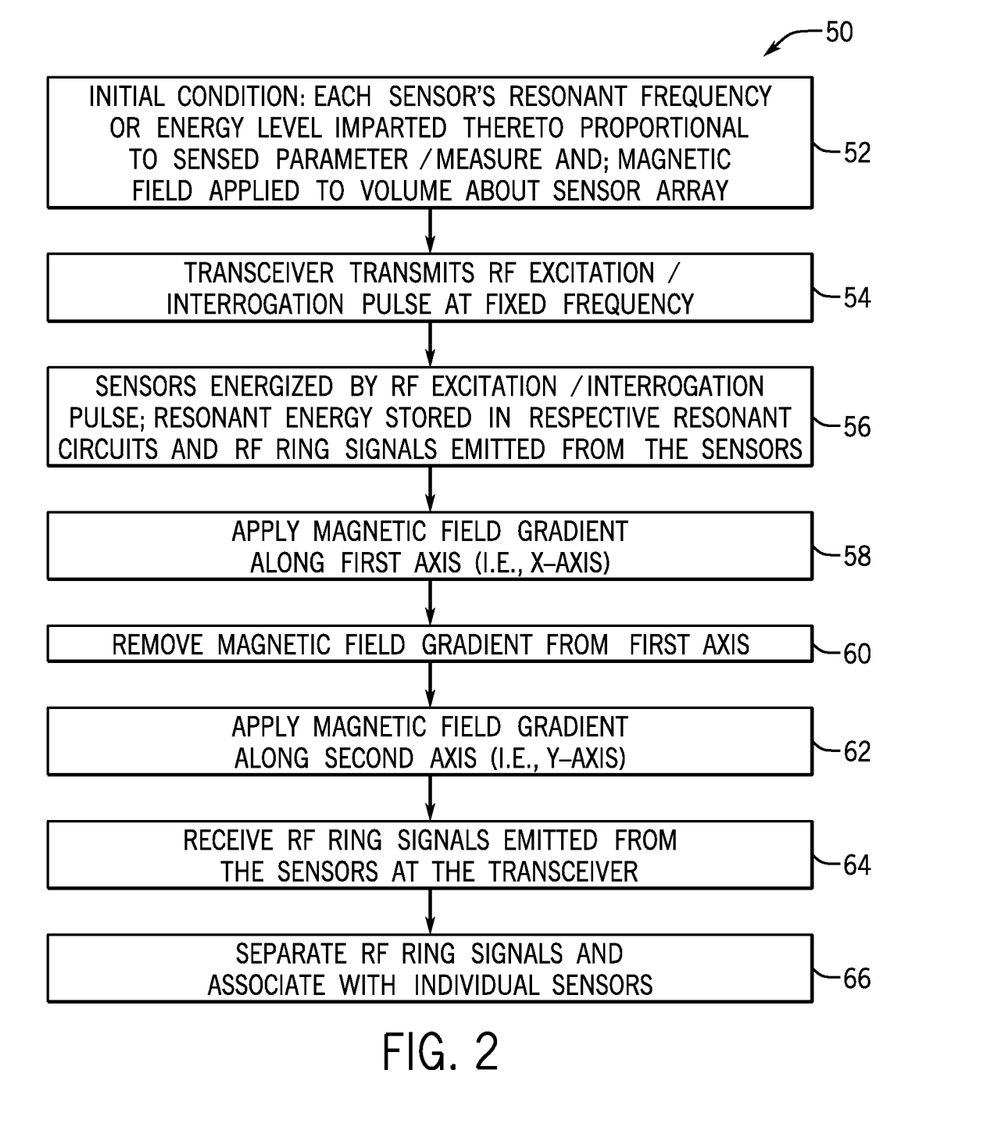
FIG. 2 is a flowchart illustrating a technique for interrogating the plurality of wireless resonant sensors in the passive wireless sensor array communication system of FIG. 1 in accordance with an embodiment of the invention.

Referring now to FIG. 2, and with continued reference to FIG. 1, a flow diagram illustrating a technique 50 for interrogating the plurality of wireless resonant sensors 16 in the sensor array 14 is shown according to an embodiment of the invention. The technique 50 begins at STEP 52 with the sensors 16 being in an initial condition where the sensors 16 are already configured such that, for each sensor, the resonant frequency is proportional to the sensed parameter, such as neural activity for example, although parameters such as pressure, temperature, acceleration, angular rate, PH level, glucose level, salinity, viscosity, dielectric constant, humidity, proximity, electrolyte level, or other know parameters could instead be measured. The sensor 16 is designed to have an operating frequency range that maps to a range of values of the sensed parameter. An additional state or parameter of the initial condition of the sensors 16 at STEP 52 is that a magnetic field is present in the volume 40 in which the sensor array 14 is positioned. Accordingly, at STEP 52, the controller 42 of interrogator system 12 controls the magnet 36 of magnet—gradient coil arrangement 34 to generate a uniform magnetic field (polarizing field $B_0$) for the volume 40.

When it is desired to acquire readings from the sensors 16 of the sensor array 14, the transceiver 18 may transmit an RF excitation/interrogation pulse 22 in the vicinity of the sensors 16 at STEP 54. The RF pulse 22 may be a brief burst of energy at a predetermined fixed frequency. The RF pulse 22 frequency may be selected to be at or near the middle of the operating frequency range of the sensors 16, and the bandwidth of the RF pulse may be narrow. An advantage of a narrow bandwidth pulse is that it is less likely to interfere electromagnetically with other devices around it. A further advantage of a narrow bandwidth pulse is that it allows the wireless sensor array communication system 10 to comply more readily with government or industry regulations regarding electromagnetic spectrum allocation, by enabling system designers to select a pulse frequency within a tight band specified by such regulations. In one embodiment, the RF pulse 22 is narrow and centered at 13.56 MHz, which is one of the so-called Industrial, Scientific, and Medical (ISM) bands allocated for use in commercial RF devices by the International Telecommunications Union (ITU)—with a benefit of a low RF frequency such as 13.56 MHz being that the wavelength is relatively long, and therefore it will penetrate deeper and over longer distances when the effective coupling to the sensors is longer. Yet another advantage of a narrow bandwidth pulse is that it may require less power than an equivalent continuous-transmit solution, thus making transceiver 18 more amenable to battery operation, and allowing the use of smaller components which generally require less heatsinking than their higher powered counterparts. Finally, an advantage of transmitting a fixed frequency RF pulse 22 at STEP 54 is that the transmit circuitry of transceiver 18 is simple compared to swept-frequency or continuous-transmit solutions.

Because the sensors 16 of sensor array 14 are positioned within a volume 38 in close proximity to transceiver 18, the sensors 16 are each energized simultaneously by RE pulse 22 at STEP 56 via inductive coupling between their respective antenna (i.e., inductor 26) and that of transceiver 18. The RF pulse 22 causes current to flow in the resonant circuit 24 of each sensor 16, energizing the resonant circuit formed by inductor 26 and capacitor 28. The resonant energy stored in the resonant circuit 24 of sensor 16 oscillates at the resonant frequency of the sensor 16, with the resonant energy being emitted by the sensor at this frequency as an RIP ring signal 20, as further indicated at STEP 56. It is recognized that the RF pulse 22 is generally of short duration and that the resonant energy stored in the resonant circuit 24 of sensor 16 begins to dissipate upon termination of the RF pulse 22, oscillating at the resonant frequency of the sensor 16 as it does so and being emitted by the sensor at this frequency as the RF ring signal 20. It is further recognized that, after terminating transmission of the RF pulse 22, the transceiver 18 then immediately goes into a receiving mode in order to provide for detection of the RF ring signals 22 from the sensors 16.

Upon transmission of the RF excitation/interrogation pulse 22 at STEP 54 and the subsequent energizing of the sensors 16 at STEP 56, the technique 50 continues at STEP 58 by applying a magnetic field gradient to the magnetic field in volume 40 along a first axis, i.e., an X-axis. To apply the magnetic field gradient along the first axis, the controller 42 of interrogator system 12 sends control signals to the gradient coil assembly 38 to selectively excite the first gradient coil 44, thereby selectively generating a magnetic field gradient along the first axis. Application of the magnetic field gradient along the first axis causes a material characteristic of the magnetic component 32 to be altered—such as an inductance of the magnetic component 32 (when formed of a resonant material)—with the altering of the inductance being based on a local magnetic field strength of the magnetic field at a location of the sensor 16 within the magnetic field. The altered inductance of the component 32 in turn causes a frequency of the RF ring signal emitted by each sensor 16 to be shifted or altered proportional to the local magnetic field strength present at the location of each respective sensor. That is, the shifting of the frequency of the RF ring signal emitted by a respective sensor 16 will differ from the shifting of the frequency of the RF ring signal emitted by other respective sensors 16 in the sensor array 14 based on the location of each of the sensors 16 in the volume 40.

In a next step of technique 50, the magnetic field gradient along the first axis is subsequently removed, as indicated at STEP 60. Removal of the magnetic field gradient along the first axis restores the magnetic field to its original condition, i.e., a uniform magnetic field. The removal of the magnetic field gradient along the first axis thus also removes the frequency shift from the RF ring signals emitted by the sensors 16 of the sensor array 14 that was induced by the magnetic field gradient along the first axis. While the frequency shift of the RF ring signals emitted by the sensors 16 is removed upon termination of the magnetic field gradient (such that the sensors are emitting RF ring signals at the same frequency), the RF ring signals 20 emitted from the sensors 16 are emitted with different phases due to the application and subsequent removal of the magnetic field gradient along the first axis.

The technique 50 next continues at STEP 62 by applying a magnetic field gradient to the magnetic field in volume 40 along a second axis, i.e., a Y-axis. To apply the magnetic field gradient along the second axis, the controller 42 of interrogator system 12 sends control signals to the gradient coil assembly 38 to selectively excite the second gradient coil 46, thereby selectively generating a magnetic field gradient along the second axis. Application of the magnetic field gradient along the second axis again causes a material characteristic of the magnetic component 32 to be altered—such as the inductance of the magnetic component 32 (when formed of a resonant material)—with the altering of the inductance being based on a local magnetic field strength of the magnetic field at a location of the sensor 16 within the magnetic field. The altered inductance of the component 32 in turn causes a frequency of the RF ring signal emitted by each sensor 16 to be shifted or altered proportional to the local magnetic field strength present at the location of each respective sensor. That is, the shifting of the frequency of the RF ring signal emitted by a respective sensor 16 will differ from the shifting of the frequency of the RF ring signal 20 emitted by other respective sensors 16 in the sensor array 14 based on the location of each of the sensors 16 in the volume 40.

Upon application of the magnetic field gradient along the second axis at STEP 62, and the associated location dependent frequency shift of the RF ring signal 20 generated by each sensor 16 caused thereby, the RF ring signal 20 emitted by each sensor 16 will have a unique phase-frequency pair. The RF ring signal 20 emitted by each sensor 16 having its own unique phase-frequency pair is received by the transceiver 18 at STEP 64 and, upon acquisition of a sufficient number of RF ring signals from each sensor 16, the transceiver functions to separate the signals received from the sensors 16 at STEP 66 and associate each RF ring signal with a particular wireless sensor 16 based on the spatial encoding provided by the unique phase-frequency pair of each RF signal. In separating the signals received from the sensors 16 and associating each RF ring signal with a particular wireless sensor 16 at STEP 66, the transceiver 18 is programmed to solve a series of simultaneous equations and/or perform an inverse Fourier transform (which can be one, two or three dimensional depending on the technique used to excite the sensors) as part of performing an imaging technique to generate an image of the outputs of the sensors 16 and thereby allow for separation and association of the individual sensor outputs.

To provide further clarification regarding the performing of STEPS 58-66 for spatially encoding RF ring signals 22 provided by the sensors 16 and using the spatially encoded signals to separate signals from each sensor, a more detailed description of spatial encoding is provided here below. It is recognized that the task of spatial encoding is to vary frequency $\omega(x, y, z, t)$ and phase $\phi(x, y, z, t)$ over a volume (e.g., volume 40 containing sensors 16 at varying locations therein) for every measurement in such a way that the original distribution of magnetization $M_{xy}(x, y, z, t)$ can be recovered from a set of integrals. This is achieved by applying a spatially variable (stationary in time) magnetic field $B'_0(x, y, z) = B'_0(x, y, z)\hat{z}$ that induces spatial distribution of Larmor frequencies over the volume. Spatial derivatives of $B'_0(x, y, z)$ are hereafter denoted as $(G_x, G_y, G_z)$. Spatial encoding can be achieved via phase encoding and frequency, with the encoding being performed after the RF excitation/interrogation pulse has been transmitted to the sensors 16 and the sensors are generating RF ring signals 20.

To perform a phase encoding operation, a linear field of gradient $G_y$ is applied such that a Larmor frequency distribution will also be linear in y. This will cause variation in the phase of magnetization. After time $\tau$, the phase of point (x, y) is determined by $$\phi(x,y)=(\omega(x,y)-\omega_0)\tau=\gamma G_y y\tau \quad \text{[Eqn. 1]}.$$

After the gradient is switched off, the precession frequency returns to a constant value over the plane, while the phase remains proportional to y.

In performing a frequency encoding operation, if a constant gradient $G_x$ is applied, the frequency of precession will change linearly with location:

$$\omega(x,y)=\gamma G_x x \quad \text{[Eqn. 2]}.$$

If the signal is read off while this gradient is on, contributions of sensors at different locations will have different frequencies.

If three encoding steps are performed after the beginning of the frequency encoding pulse $G_x$, the transverse magnetization of a sensor (x, y) in the excited plane is given by:

$$M_{xy}(x,y,t)=M^{\hat{}}_{xy}(x,y,t)e^{j(\omega(x,y,t)t+\phi(x,y,t))}=M^{\hat{}}_{xy}(x,y,t)e^{j(\gamma G_x x t + \gamma G_y y \tau)} \quad \text{[Eqn. 3]},$$

inducing a signal $$S(t)=\iint M_{xy}(x,y,t)dxdy=\iint M^{\hat{}}_{xy}(x,y,t)e^{j(\gamma G_x x t + \gamma G_y y \tau)}dxdy \quad \text{[Eqn. 4]}.$$

If we denote $$k_x=-\gamma G_x t, k_y=-\gamma G_y \tau \quad \text{[Eqn. 5]},$$

then $$S(t)=S(k_x(t),k_y)=\iint M^{\hat{}}_{xy}(x,y,t)e^{-j(k_x x + k_y y)}dxdy=F_{M^{\hat{}}}(k_x,k_y) \quad \text{[Eqn. 6]},$$

where $F_{M^{\hat{}}}$ is the Fourier transform of the magnetization at time t. The phase and the frequency encoding steps essentially "tag" every sensor location with a distinct pair of a phase and a frequency of the magnetization precession. The integral of this pattern is the Fourier transform of the magnetization. The signal measured during one such iteration produces a row in the spatial frequency space $(k_x, k_y)$. After repeating this process several times for different values of $G_y$ and completing matrix $S(k_x, k_y)$, the image of transverse magnetization can be recovered by applying the inverse discrete Fourier transform.

Beneficially, embodiments of the invention thus provide wireless resonant sensors useable as part of a sensor array that may be interrogated via the use of a combination of RF pulses and magnetic field gradients being applied thereto, such that each resonant sensor will emit a unique phase and frequency pair based on its positioning within the magnetic field. The unique phase and frequency pair emitted from each sensors responsive to the applied RF pulses and magnetic field gradients allows for each sensor to be uniquely identified and differentiated from other resonant sensors in the sensor array. The resonant sensors in the sensors array have a common construction and do not require complex signal processing electronics therein, such that the cost and complexity of the resonant sensors is minimized.

A technical contribution of embodiments of the invention is that it provides a controller implemented technique for interrogating an array of resonant sensors by applying a combination of RF pulses and magnetic field gradient along a number of axes. The selective application of the magnetic field gradients causes each resonant sensor to emit an RF ring signal having a unique phase and frequency pair that is based on its positioning within the magnetic field, so as to enable the reading of each sensor to be separated at a transceiver.

Therefore, according to one embodiment of the invention, a wireless sensor array communication system includes a sensor array composed of a plurality of wireless sensors, each of the plurality of wireless sensors comprising a resonant circuit that is excited responsive to an RF pulse received by the wireless sensor such that the resonant circuit provides a resonant energy, with a characteristic of the resonant energy being proportional to a measurand monitored by the passive wireless sensor. The wireless sensor array communication system also includes an interrogator system having a transceiver in operable communication with each of the plurality of wireless sensors in the sensor array, with the transceiver configured to transmit RF pulses to each of the plurality of wireless sensors to excite the respective resonant circuits therein and receive RF signals transmitted from each of the plurality of wireless sensors in the sensor array, each of the RF signals being indicative of the resonant energy provided by the resonant circuit. The interrogator system further includes a magnet-gradient coil arrangement configured to generate a magnetic field and selectively apply magnetic field gradients to the magnetic field along a number of axes. Each of the plurality of wireless sensors is configured such that a frequency and phase of the resonant energy provided by its respective resonant circuit, and included in the RF signal transmitted therefrom, is altered responsive to the generated magnetic field and the applied magnetic field gradients, the altered frequency and phase of the resonant energy being a function of a location of the respective wireless sensor within the magnetic field.

According to another embodiment of the invention, a method of interrogating a plurality of wireless sensors in a sensor array includes wirelessly transmitting an RF pulse from a transceiver to each of the plurality of wireless sensors in the sensor array, the RF pulse exciting a resonant circuit included in each of the plurality of wireless sensors so as to cause the resonant circuit to generate a resonant energy. The method also includes applying a magnetic field to a volume including the sensor array via a magnet, applying a magnetic field gradient to the magnetic field along a first axis via activation of a first gradient coil, applying a magnetic field gradient to the magnetic field along a second axis via activation of a second gradient coil, and wirelessly transmitting RF signals from each of the plurality of wireless sensors in the sensor array as sensor outputs to the transceiver, with the RF signal transmitted from each respective wireless sensor indicative of the resonant energy generated by its respective resonant circuit. Application of the magnetic field gradient along the first and second axes causes a frequency and phase of the RF signal generated by each respective wireless sensor of the plurality of wireless sensors to be altered as a function of a location of the respective wireless sensor within the volume to which the magnetic field is applied.

According to yet another embodiment of the invention, a passive wireless sensor includes an antenna configured to receive RF interrogation pulses and transmit RF signals and a resonator circuit operably connected to the antenna and that is excited responsive to RF interrogation pulses received by the antenna, the resonator circuit configured to generate a resonant energy responsive to an RF interrogation pulse, with the resonant energy being proportional to a parameter monitored by the passive wireless sensor. The passive wireless sensor also includes a magnetic component incorporated into the resonator circuit that is sensitive to a magnetic field such that a material characteristic of the magnetic component is altered when exposed to a magnetic field, with the magnetic component being constructed so as to alter a frequency of the resonant energy generated by the resonator circuit when selectively exposed to a magnetic field and magnetic field gradients, wherein the altering of the frequency and phase of the resonant energy is based on a local magnetic field strength of the magnetic field at a location of the passive wireless sensor within the magnetic field.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A wireless sensor array communication system comprising:
   a sensor array composed of a plurality of wireless sensors, each of the plurality of wireless sensors comprising a resonant circuit that is excited responsive to an RF pulse received by the wireless sensor such that the resonant circuit provides a resonant energy, with a characteristic of the resonant energy being proportional to a measurand monitored by the passive wireless sensor; and
   an interrogator system comprising:
      a transceiver in operable communication with each of the plurality of wireless sensors in the sensor array, the transceiver configured to:
         transmit RF pulses to each of the plurality of wireless sensors to excite the respective resonant circuits therein; and
         receive RF signals transmitted from each of the plurality of wireless sensors in the sensor array, each of the RF signals being indicative of the resonant energy provided by the resonant circuit; and
      a magnet-gradient coil arrangement configured to generate a magnetic field and selectively apply magnetic field gradients to the magnetic field along a number of axes;
   wherein each of the plurality of wireless sensors is configured such that a frequency and phase of the resonant energy provided by the resonant circuit therein, and included in the RF signal transmitted therefrom, is altered responsive to the generated magnetic field and the applied magnetic field gradients, the altered frequency and phase of the resonant energy being a function of a location of the respective wireless sensor within the magnetic field.

2. The wireless sensor array communication system of claim 1 wherein the resonant circuit of a respective wireless sensor comprises a magnetic component that is sensitive to the magnetic field generated by the magnet-gradient coil arrangement, such that a material characteristic of the magnetic component is altered when exposed to the magnetic field.

3. The wireless sensor array communication system of claim 2 wherein the material characteristic of the magnetic component that is altered when exposed to the magnetic field comprises an inductance of the magnetic component, with the altered inductance of the magnetic component causing a frequency of the resonant energy provided by its respective resonant circuit to be altered.

4. The wireless sensor array communication system of claim 1 wherein the interrogation system further comprises a controller configured to control the magnet-gradient coil arrangement to generate the magnetic field and selectively apply the magnetic field gradients to the magnetic field along the number of axes.

5. The wireless sensor array communication system of claim 4 wherein the controller is configured to:
control the magnet-gradient coil arrangement to selectively apply a magnetic field gradient to the magnetic field along each of a first axis and along a second axis; and
control the magnet-gradient coil arrangement to remove the magnetic field gradient along the first axis prior to applying the magnetic field gradient to the magnetic field along the second axis.

6. The wireless sensor array communication system of claim 5 wherein application of the magnetic field gradient along the first axis shifts the frequency of the resonant energy generated by the respective wireless sensor proportional to a local magnetic field strength at the respective wireless sensor;
wherein removal of the magnetic field gradient along the first axis removes the frequency shift from the resonant energy provided by the respective wireless sensor, but alters the phase of the resonant energy; and
wherein application of the magnetic field gradient along the second axis shifts the frequency of the resonant energy provided by the respective wireless sensor proportional to the local magnetic field strength at the respective wireless sensor, such that the respective wireless sensor thus generates a resonant energy with a unique phase-frequency pair.

7. The wireless sensor array communication system of claim 6 wherein the transceiver is further configured to associate each RF signal received at the transceiver with a particular wireless sensor of the plurality of wireless sensors based on the frequency and phase of each RF signal received thereby.

8. The wireless sensor array communication system of claim 7 wherein, in associating each RF signal with a particular wireless sensor of the plurality of sensors, the transceiver is configured to:
receive a plurality of RF signals from each of the plurality of wireless sensors at the transceiver; and
form an image of an output of the sensor array based on the received plurality of RF signals from each of the plurality of wireless sensors.

9. The wireless sensor array communication system of claim 1 wherein the transceiver is configured to transmit RF pulses to all of the plurality of wireless sensors simultaneously, so as to excite the respective resonant circuits therein in a simultaneous manner.

10. The wireless sensor array communication system of claim 1 wherein the plurality of wireless sensors in the sensor array are configured to measure neural activity of a brain.

11. A method of interrogating a plurality of wireless sensors in a sensor array, the method comprising:
wirelessly transmitting an RF pulse from a transceiver to each of the plurality of wireless sensors in the sensor array, the RF pulse exciting a resonant circuit included in each of the plurality of wireless sensors so as to cause the resonant circuit to generate a resonant energy;
applying a magnetic field to a volume including the sensor array via a magnet;
applying a magnetic field gradient to the magnetic field along a first axis via activation of a first gradient coil;
applying a magnetic field gradient to the magnetic field along a second axis via activation of a second gradient coil; and
wirelessly transmitting RF signals from each of the plurality of wireless sensors in the sensor array as sensor outputs to the transceiver, with the RF signal transmitted from each respective wireless sensor indicative of the resonant energy generated by the resonant circuit therein;
wherein application of the magnetic field gradient along the first and second axes causes a frequency and phase of the RF signal generated by each respective wireless sensor of the plurality of wireless sensors to be altered as a function of a location of the respective wireless sensor within the volume to which the magnetic field is applied.

12. The method of claim 11 wherein application of the magnetic field gradient along the first and second axes alters a material characteristic of a magnetic component in the resonant circuit that is sensitive to the magnetic field generated by the magnet.

13. The method of claim 12 wherein the material characteristic of the magnetic component that is altered when exposed to the magnetic field comprises an inductance of the magnetic component, with the altered inductance of the magnetic component causing a frequency of the resonant energy generated by its respective resonant circuit to be altered.

14. The method of claim 11 further comprising removing the magnetic field gradient along the first axis prior to applying the magnetic field gradient to the magnetic field along the second axis.

15. The method of claim 14 wherein application of the magnetic field gradient along the first axis shifts the frequency of the resonant energy generated by the respective wireless sensor proportional to a local magnetic field strength at the respective wireless sensor;
wherein removal of the magnetic field gradient along the first axis removes the frequency shift from the resonant energy generated by the respective wireless sensor, but alters the phase of the resonant energy; and
wherein application of the magnetic field gradient along the second axis shifts the frequency of the resonant energy generated by the respective wireless sensor proportional to the local magnetic field strength at the respective wireless sensor, such that the respective wireless sensor thus generates a resonant energy with a unique phase-frequency pair.

16. The method of claim 15 further comprising associating each RF signal received at the transceiver with a particular wireless sensor of the plurality of sensors based on the unique phase-frequency pair of each RF signal.

17. The method of claim 16 wherein associating each RF signal with a particular wireless sensor of the plurality of sensors comprises:

receiving a plurality of RF signals from each of the plurality of wireless sensors at the transceiver; and generating an image of the sensor outputs from the received plurality of RF signals, including solving a series of simultaneous equations or performing an inverse Fourier transform in order to form the image of the sensor outputs.

18. A passive wireless sensor comprising:

an antenna configured to receive RF interrogation pulses and transmit RF signals;

a resonator circuit operably connected to the antenna and that is excited responsive to RF interrogation pulses received by the antenna, the resonator circuit configured to generate a resonant energy responsive to an RF interrogation pulse, with the resonant energy being proportional to a parameter monitored by the passive wireless sensor; and a magnetic component incorporated into the resonator circuit that is sensitive to a magnetic field such that a material characteristic of the magnetic component is altered when exposed to a magnetic field;

wherein the magnetic component is constructed so as to alter a frequency of the resonant energy generated by the resonator circuit when selectively exposed to a magnetic field and magnetic field gradients generated by a magnet-gradient coil arrangement, wherein the altering of the frequency and phase of the resonant energy is based on a local magnetic field strength of the magnetic field at a location of the passive wireless sensor within the magnetic field.

19. The passive wireless sensor of claim 18 wherein the resonator circuit comprises a capacitor-inductor arrangement that generates a resonant energy when excited by the RF interrogation pulses.

20. The passive wireless sensor of claim 19 wherein the material characteristic of the magnetic component that is altered when exposed to the magnetic field comprises an inductance of the magnetic component, with the altered inductance of the magnetic component causing a frequency of the resonant energy generated by the resonator circuit to be altered.

* * * * *